United States Patent [19]
Bennett et al.

[11] Patent Number: 5,669,070
[45] Date of Patent: Sep. 23, 1997

[54] EYE PROTECTION FOR WELDING

[76] Inventors: Jonathan Bennett, 690 Joseph St., R.R. #1 Peterborough, Ontario, Canada, K9J 6X2; Reagh Mann, Post Office Fraserville, Ontario, Canada, K0L 1V0

[21] Appl. No.: 548,521

[22] Filed: Oct. 26, 1995

[51] Int. Cl.⁶ .......................................... A61F 9/06
[52] U.S. Cl. ................................................ 2/8
[58] Field of Search ........................ 2/8, 15, 10, 9, 2/424

[56] References Cited

U.S. PATENT DOCUMENTS

| | | | |
|---|---|---|---|
| 2,618,781 | 11/1952 | Beauverger | 2/8 |
| 2,644,159 | 7/1953 | Jacobs | 2/8 |
| 2,644,160 | 7/1953 | Jacobs | 2/8 |
| 3,332,087 | 7/1967 | Manz | 2/8 |
| 3,868,727 | 3/1975 | Paschall | 2/8 |
| 4,155,122 | 5/1979 | Budmiger | 2/8 |
| 4,354,279 | 10/1982 | Walters, Jr. et al. | 2/8 |

*Primary Examiner*—Michael A. Neas

[57] ABSTRACT

Disclosed herein is a welding helmet, comprising a face-protecting shroud, the shroud having an aperture, the shroud including a filter for protecting an operator from potentially damaging radiant energy being emitted from a workpiece, the filter providing a first viewing region through which the operator may safely view the workpiece during activities generating potentially damaging radiant energy, and a second viewing region adjacent the first viewing region for viewing the workpiece during activities not generating potentially damaging radiant energy, thereby allowing the operator to view the workpiece through either one of the viewing areas without the need to remove the welding helmet.

3 Claims, 5 Drawing Sheets

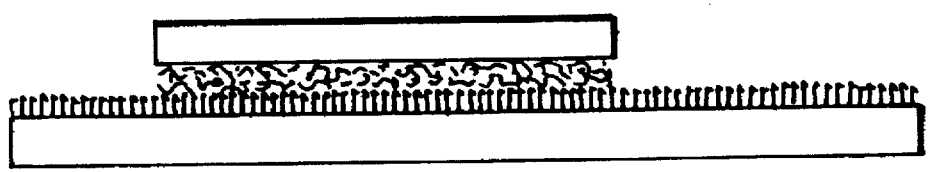
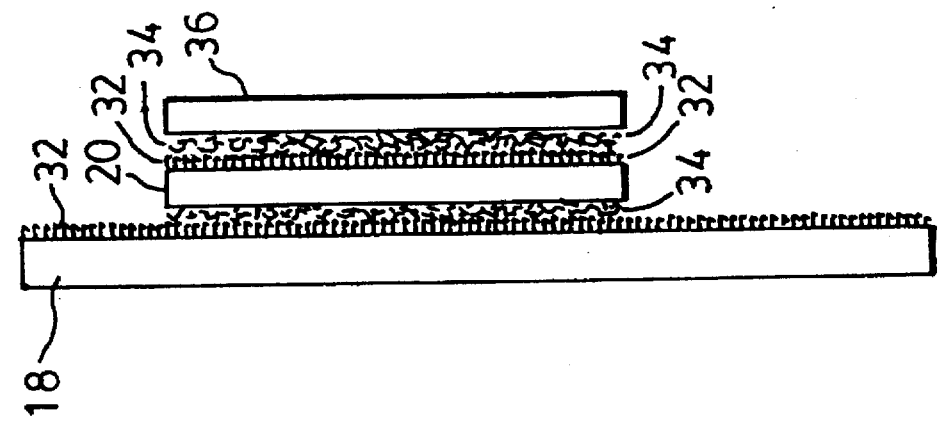
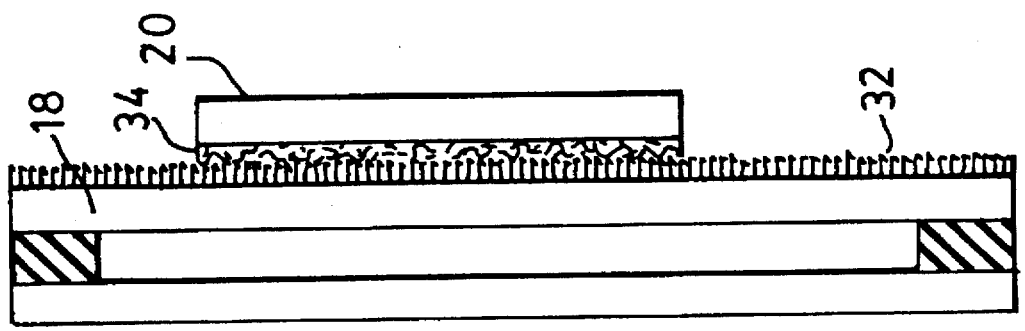

EYE PROTECTION FOR WELDING

BACKGROUND OF THE INVENTION

1. Field of the Invention

The present invention relates to welding helmets.

2. Description of the Related Art

It is common knowledge in the welding industry that filter plates of various shades are used in welding helmets to protect the operator's eyes from the effects of harmful radiant energy including rays of light produced by various forms of welding.

Industry standard lenses are numbered using a well known rating index known as Luminous Transmittance, specifically from 1.5 to 14, the higher the number the darker the shade and the greater the protection from harmful rays of light. The shade number chosen for a particular welding process is determined by the welding process being used, the heat being applied, the metals that are being welded and a personal preference of the welding operator.

Tests have shown that a shade number ten will provide sufficient protection for most electric welding processes, however shades ten to thirteen are most common.

Filter plates commonly used admit very little ambient light when the welding arc is off. Therefore, the operator must manually raise and lower the helmet in order to set up for the next weld. This manual operation is carried out dozens of times per working day, and in rare cases has proven to be the cause of neck strains and similar muscular disorders. In addition, valuable time is consumed during the positioning of the helmet in preparation for viewing of the next weld.

It is therefore an object of the present invention to obviate or mitigate the above mentioned disadvantages.

SUMMARY OF THE INVENTION

Briefly stated, the invention involves a welding helmet, comprising a face-protecting shroud, the shroud having an aperture, the shroud including filter means for protecting an operator from potentially damaging radiant energy being emitted from a workpiece, the filter means providing a first viewing region through which the operator may safely view the workpiece during activities generating potentially damaging radiant energy, and a second viewing region adjacent the first viewing region for viewing the workpiece during activities not generating potentially damaging radiant energy, thereby allowing the operator to view the workpiece through either one of the viewing areas without the need to remove the welding helmet.

In another aspect of the present invention, there is provided a filter assembly for a welding helmet of a type having a face-protecting shroud, the shroud having an aperture for receiving a radiant energy filter therein for protecting an operator from potentially damaging radiant energy being emitted from a workpiece, the filter assembly comprising a first filter plate portion arrangement which is arranged to provide a first viewing region through which the operator may safely view the workpiece during activities generating potentially damaging radiant energy, and a second filter plate portion arrangement which is arranged to provide a second viewing region adjacent the first viewing region for viewing the workpiece during activities not generating potentially damaging radiant energy, thereby allowing the operator to view the workpiece through either one of the viewing areas without the need to remove the welding helmet.

In still another aspect of the present invention, there is provided a kit for a welding helmet of a type having a face-protecting shroud, the shroud having an aperture for receiving a radiant energy filter therein for protecting an operator from potentially damaging radiant energy being emitted from a workpiece, the kit comprising at least one filter plate portion for use in the aperture so as to provide a first viewing region through which the operator may safely view the workpiece during activities generating potentially damaging radiant energy, and a second viewing region adjacent the first viewing region for viewing the workpiece during activities not generating potentially damaging radiant energy, and a set of instructions for the installation of the kit thereby to allow the operator to view the workpiece through either one of the viewing areas without the need to remove the welding helmet.

In still another aspect of the present invention, there is provided a method of improving a welding helmet, comprising the steps of:

providing a helmet having a face-protecting shroud with an aperture; and positioning in the shroud a filter assembly providing a first viewing region through which an operator may safely view a workpiece during activities generating potentially damaging radiant energy, and a second viewing region adjacent the first viewing region for viewing the workpiece during activities not generating potentially damaging radiant energy, thereby allowing the operator to view the workpiece through either one of the viewing areas without the need to remove the welding helmet.

BRIEF DESCRIPTION OF THE DRAWINGS

Several preferred embodiments of the present invention will now be described, by way of example only, with reference to the appended drawings in which:

FIG. 4 is a side view of the two components of FIGS. 2 and 3 in an assembled condition;

FIG. 5a is side view corresponding to FIG. 4 including one additional component;

FIG. 5b is another side view corresponding to 5a with the additional component in an another configuration; and FIG. 5c is a perspective assembly of the components illustrated in FIG. 5a.

DESCRIPTION OF THE PREFERRED EMBODIMENTS

Referring to the figures, there is provided a welding helmet 10 having a face-protecting shroud 12 with an aperture shown at 14. As will be described, the shroud includes filter means in the form of a filter assembly 16 for protecting an operator from potentially damaging radiant energy being emitted from a workpiece. The filter assembly provides a first viewing region shown at 'A' through which the operator may safely view the workpiece during activities generating potentially damaging radiant energy, as well as a second viewing region 'B' adjacent the first viewing region for viewing the workpiece during activities not generating potentially damaging radiant energy, thereby allowing the operator to view the workpiece through either one of the viewing areas without the need to remove the welding helmet.

Figure 1:
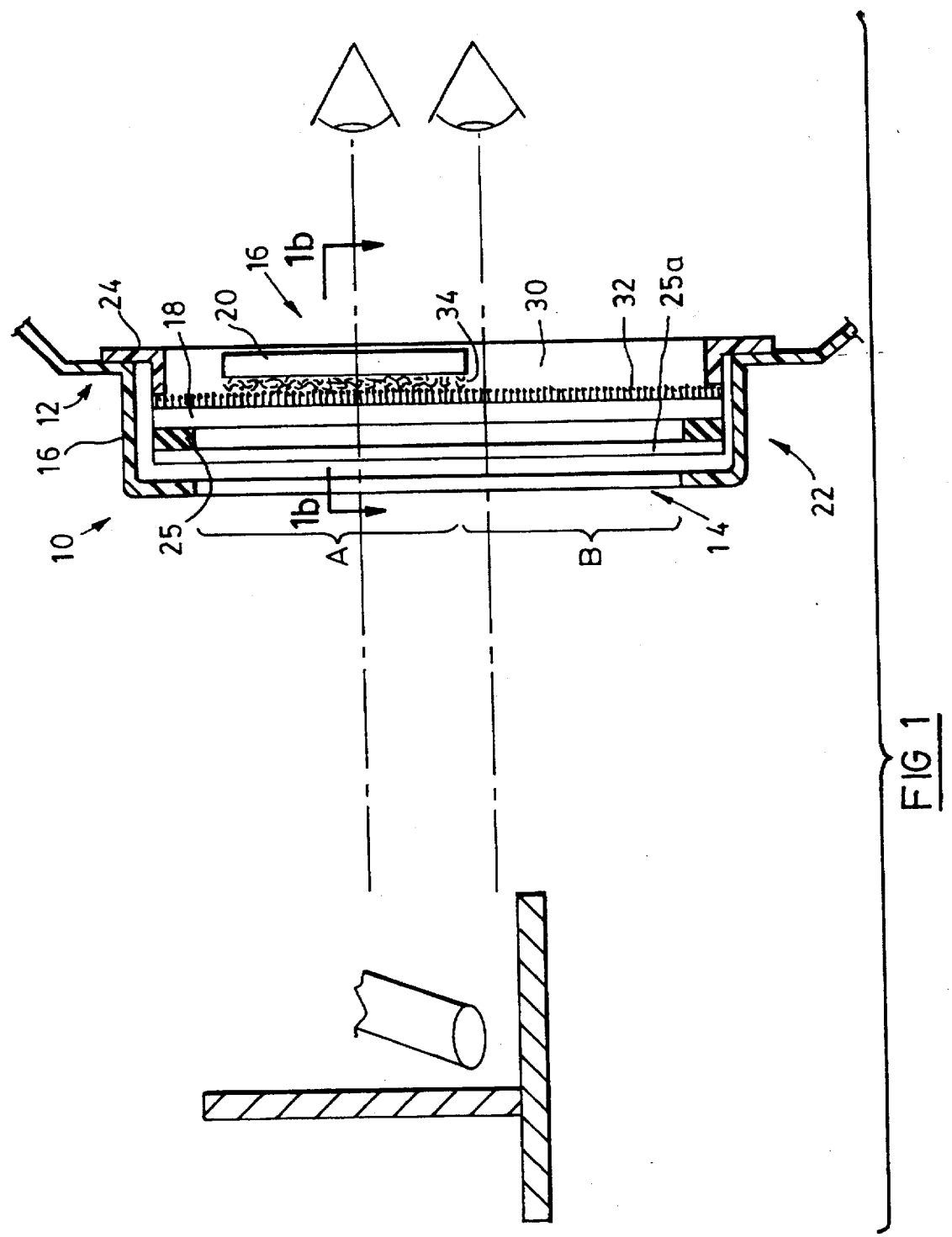
FIG. 1 is a schematic view of a welding helmet and a workpiece illustrating an optical path therebetween.
Figure 1A:
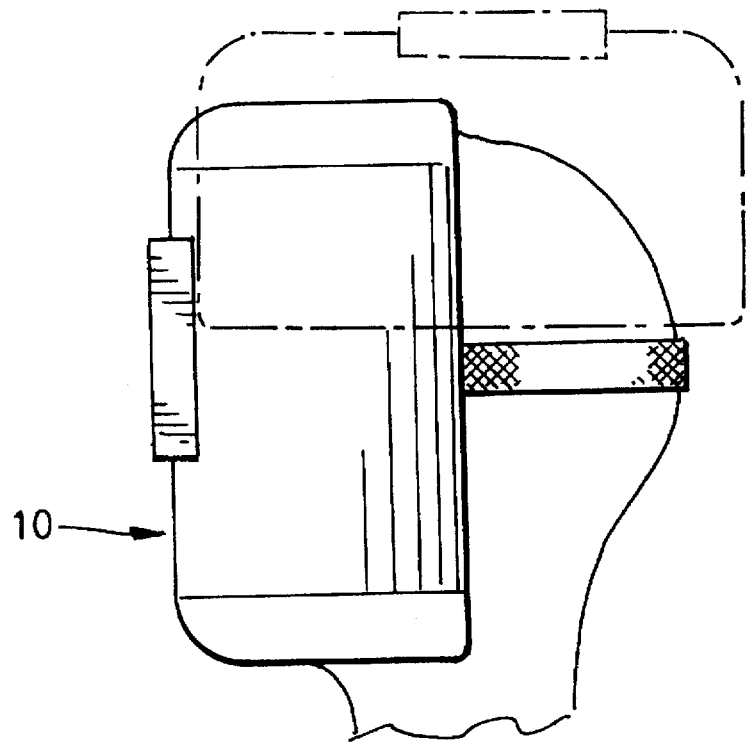
FIG. 1a is a view of a the welding helmet of FIG. 1 in an operative position.

The shroud is rotatable from an operating position as shown in figure 1a, that is in front of the eyes of the welding operator, and an inoperative position which is typically above the forehead of the welding operator, as shown in phantom.

The filter assembly includes a first filter plate portion 18 to provide the first viewing area. In the case of the helmet 10, the first filter plate portion is substantially equally sized with the aperture.

The helmet further comprises a second filter plate portion 20 positioned adjacent the first filter plate portion and corresponding with the first viewing region, the first filter plate portion further extending into a region corresponding to the second viewing region, whereby the first and second filter plate portions together have a sufficient filtering index to provide the protection.

A particular feature of the helmet 10 is the use of a combination of filter plate portions of different sizes. As will be described, the use of the first and second filter plate portions permits the welding operator to use the helmet 10 in a single position in front of his face and to eliminate the conventional inoperative position above his forehead.

The first filter plate portion is positioned in a filter plate-receiving housing of the helmet as shown at 22, and held therein by a suitable spring loaded retaining clip as used in conventional helmets and as shown schematically at 24 (or in some other appropriate fashion). Also located in the housing 22 is a light-sealing gasket shown at 25 and a transparent protective cover plate 25a (commonly used to protect filter plate from sparks and spatter). The helmet also has a positioning means 30 for releasably positioning the second filter plate portion relative to the first filter plate portion. In this case, the positioning means positions the second filter plate portion on the first filter plate portion.

As will be described, the helmet 10 makes use of a positioning means is in the form of a tape fastener arrangement, comprising a first tape fastener 32 attached to the first filter plate portion and a second tape fastener 34 complementary to the first tape fastener and attached to the second filter plate portion.

The first filter plate portion 18 has an inner face 18a with a pair of edges 18b. Disposed on each edge is one of a pair of pressure sensitive tape fasteners 30 of the type known as 'velcro'. The second filter plate portion 20 is also provided with an inner face 20a and two edges 20b. On each edge of the second filter plate portion 20 is a complementary tape fastener 34, thereby permitting the first and second filter plate portions 18 and 20 to be attached to one another.

Thus, the first and second filter plate portions provide a pair of adjacent viewing areas, a first viewing area for viewing a workpiece during a welding operation while protecting a welding operator's eyes from harmful rays of light therefrom, and a second viewing area for the welding operator to view a workpiece without removing the shroud.

In order to provide adequate protection from harmful rays, the helmet must provide the welding operator with a viewing area having the equivalent of shade number 12. In the case of the helmet 10, both the first and second filter plate portions have a shade number 6. In this manner, the combined filtering effect of the first and second filter plate portions, that is when the welding operator is looking through the first viewing region 'A', corresponds to shade number 12.

The uncovered portion of the first filter plate portion 18 corresponding to the secondary viewing region 'B' and permits the welding operator to view the work piece while the welding arc is off. The region 'A', permits the welder to view his work through the combined first and second filter plate portions 20 and 16 while protecting his skin from harmful rays of light while the welding arc is on.

After completing the welding step, the operator can see the results of his work through viewing region 'B' without having to lift the helmet.

Among other things, the present invention is significant in that the second filter plate portion 20 and the tape fasteners may be sold in the form of a kit, enabling the users of conventional welding helmets to retrofit those helmets to eliminate the need to lift the helmet to the inoperative position, in a simple, inexpensive manner. When using the kit, the operator need simply clean the first and second filter plate portions 16 and 20 and attach the corresponding tape fasteners to the filter plate portions. The user then may install the second filter plate portion 20 by aligning the filter plate portions and engaging the tape fasteners.

Figure 1B:
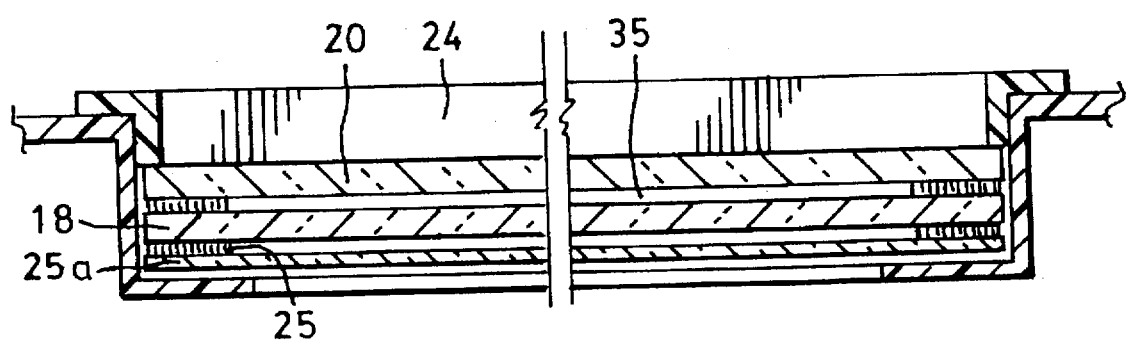
FIG. 1b is a cross sectional view taken on line 1b—1b o FIG. 1.
Figure 2:
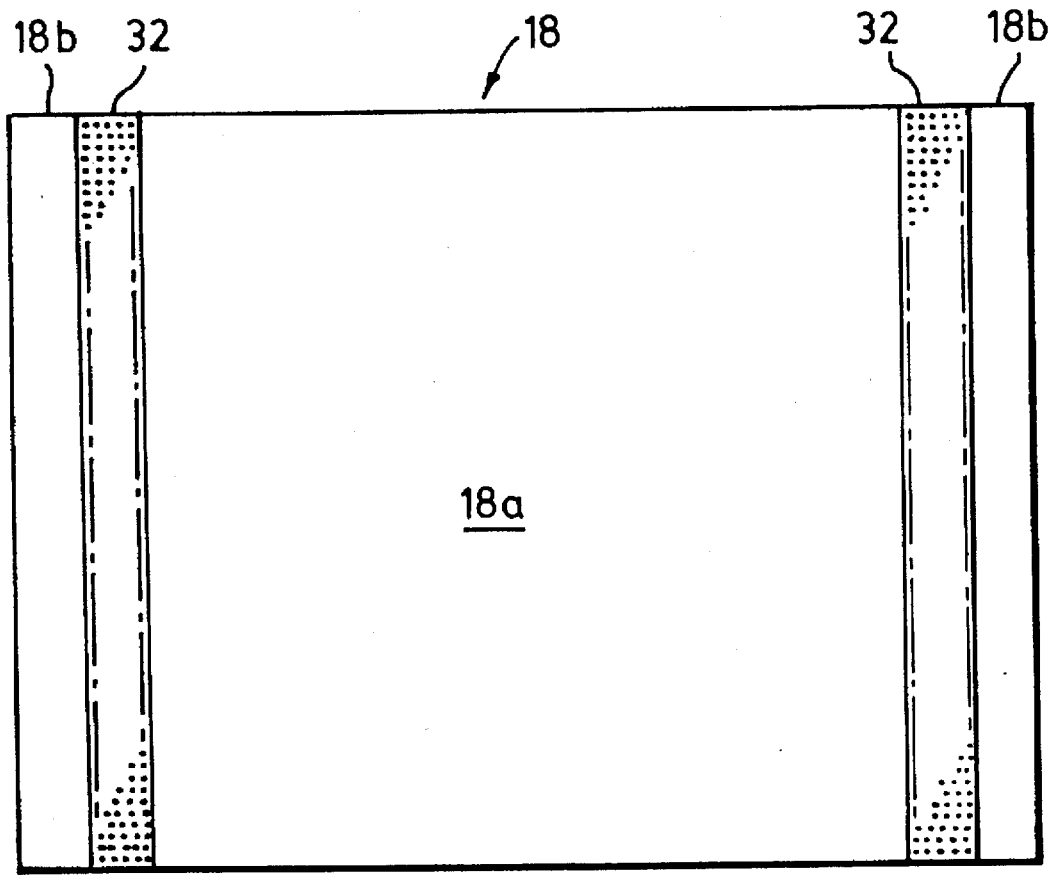
FIG. 2 is a front view of one component of the helmet illustrated in FIG. 1.
Figure 3:
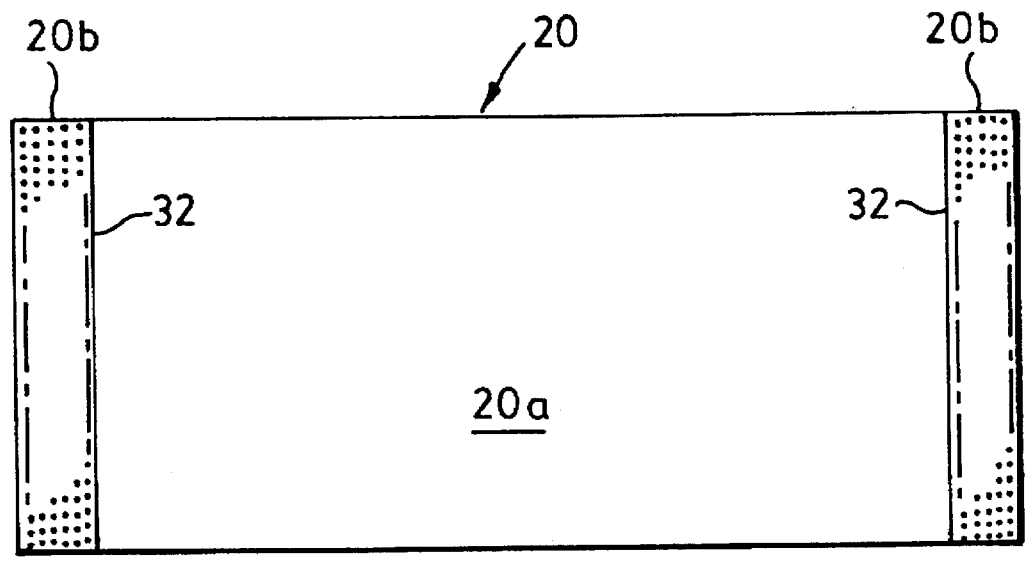
FIG. 3 is a front view of another component of the helmet illustrated in FIG. 1.

A particular feature of the present invention is the fact that, to readjust the position of the second filter plate portion 20, the user must first separate filter plate portions and then reattach them. This is advantageous because it ensures that any grime that may have built up between the plate portions during use may be removed by the operator so that no damage is caused to either filter plate portion by the grime, for example by sliding one filter plate portion relative to the other. Furthermore, the tape fasteners provide a gap between the first and second filter plate portions to minimize the build up of grime between them as shown at 35 in figure 1b.

Figure 5C:
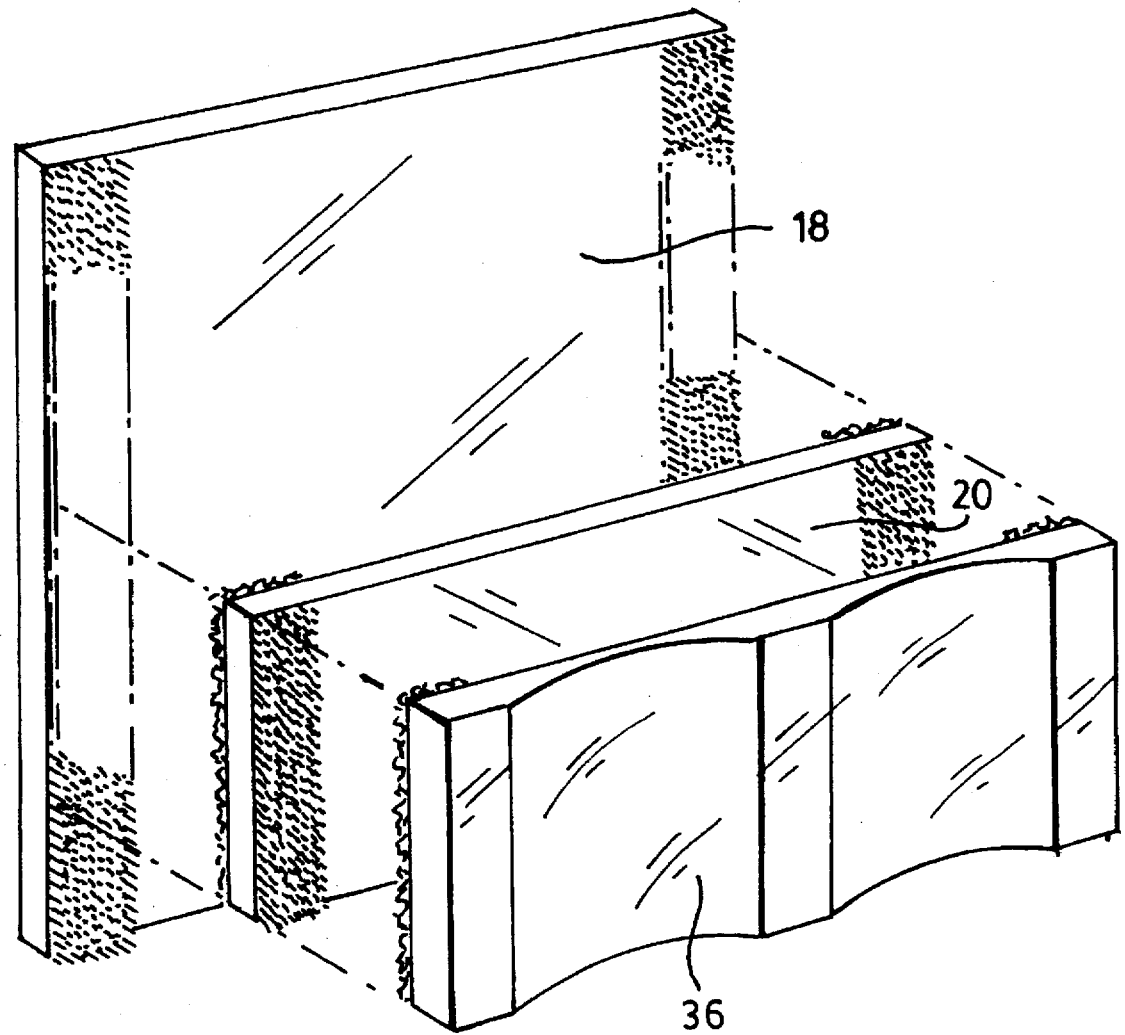

Another embodiment is shown in FIGS. 5a to 5c wherein the tape fastener is disposed on both edges of a magnifying lens 36 to the inside face of the first filter plate portion, in one case with the second filter plate portion in between and in the other case, without the use of the second filter plate portion. This embodiment is significant because the smaller magnifying lens is conventionally only usable in helmets using second filter plate portions. In this case, the smaller magnifying lens is also adjustable in the helmet enabling the welder to adjust the lens to his preference along either vision lines.

The welding helmet, and more particularly the filter plate portion combination, has numerous advantages:

i) The filter assembly is adaptable to standard welding helmets;

ii) The second filter plate portion may be repositioned over the first filter plate portion without having to remove welding gloves;

iii) A magnifying or optically corrective lens may be used in conjunction with the filter assembly simply by adding the lens to the desired location (for example as shown by FIG. 5a)

iv) Filter plate portions made from glass, polycarbonate, or other suitable materials may be used;

v) The welding helmet equipped with the filter assembly allows the welding operator to have sufficient vision and protection to view his workpiece without having to raise or remove his welding helmet;

vi) Both filter plate portions are easily removable for cleaning;

vii) The gap 35 between the filter plate portions reduces the risk of scratches caused by the presence of foreign material therebetween;

viii) The second filter plate portion may be changed quickly without dismantling the helmet;

ix) The filter assembly is time saving due to the fact that the operator does not have to manually flip the helmet up and down between the conventional operative and inoperative positions;

x) The filter assembly does not interfere with the normal assembly or operation of welding helmets;

xi) The filter plate portions are secure while being easily repositioned;

xii) The filter assembly allows the welding operator to work on 'out of position' workpieces or in physically restrictive areas where the manual raising and lowering of the welding helmet is inconvenient or impossible;

xiii) The filter assembly may be used in any eye protection or vision device where ease of removal or insertion of secondary or alternate filter plate portions or lenses is required.

While the discussion above has been restricted to the use of 'Velcro' tape fastener, it will be understood that other secure methods of attachment are also applicable including the use of a magnetic tape fastener, provided of course that the magnetic tape can generate a magnetic force sufficient to hold the second filter plate portion in position. In addition, the second filter plate portion may be attached to the inner face of the shroud 12 rather than the first filter plate portion provided that the method of attachment is such that it permits the first and second filter plate portions to be close together to avoid image distortions. The filter assembly may also be arranged to secure the second filter plate portion on the outside face of the first filter plate portion, provided that the method of attachment is sufficiently secure to prevent the second filter plate portion from being bumped off.

While the figures above relate to a welding helmet, it will be understood that the present technique may also be provided to other eye wear including other work shields.

We claim:

1. A welding helmet, comprising a face-protecting shroud, said shroud having an aperture, said shroud including filter means for protecting an operator from potentially damaging radiant energy being emitted from a workpiece, said filter means providing a first viewing region through which said operator may safely view said workpiece during activities generating potentially damaging radiant energy, and a second viewing region adjacent said first viewing region for viewing said workpiece during activities not generating potentially damaging radiant energy, thereby allowing said operator to view said workpiece through either one of said viewing areas without the need to remove said welding helmet, wherein said filter means includes a first filter plate portion to provide said first viewing area, said first filter plate portion being substantially equally sized with said aperture, said helmet further comprising a second filter plate portion positioned adjacent said first filter plate portion and corresponding with said first viewing region, said first filter plate portion further extending into a region corresponding to said second viewing region, whereby said first and second filter plate portions together have a sufficient filtering index to provide said protection, said first filter plate portion being fixed to said helmet, said helmet further comprising positioning means for releasably positioning said second filter plate portion relative to said first filter plate portion, wherein said positioning means positions said second filter plate portion on said first filter plate portion, said positioning means providing a gap to be formed between said first and second filter plates, to minimize build up of dirt between said first and second filter plates, said positioning means further comprising a tape fastener arrangement, comprising a first tape fastener attached to said first filter plate portion and a second tape fastener complementary to said first tape fastener and attached to said second filter plate portion.

2. A filter assembly for a welding helmet of a type having a face-protecting shroud, said shroud having an aperture for receiving a radiant energy filter therein for protecting an operator from potentially damaging radiant energy being emitted from a workpiece, said filter assembly comprising a first filter plate portion arrangement which is arranged to provide a first viewing region through which said operator may safely view said workpiece during activities generating potentially damaging radiant energy, and a second filter plate portion arrangement which is arranged to provide a second viewing region adjacent said first viewing region for viewing said workpiece during activities not generating potentially damaging radiant energy, thereby allowing said operator to view said workpiece through either one of said viewing areas without the need to remove said welding helmet, said filter plate portion arrangements including a first filter plate portion to contribute to said first viewing area, said first filter plate portion being substantially equally sized with said aperture, said filter plate portion arrangements including a second filter plate portion positioned adjacent said first filter plate portion and corresponding with said first viewing region, said first filter plate portion further extending into a region corresponding to said second viewing region, whereby said first and second filter plate portions together have a sufficient filtering index to provide said protection, said first filter plate portion being fixed to said helmet, said helmet further comprising positioning means for releasably positioning said second filter plate portion relative to said first filter plate portion, wherein said positioning means positions said second filter plate portion on said first filter plate portion, said positioning means further comprising a tape fastener arrangement, comprising a first tape fastener attached to said first filter plate portion and a second tape fastener complementary to said first tape fastener and attached to said second filter plate portion.

3. A kit for a welding helmet of a type having a face-protecting shroud, said shroud having an aperture for receiving a radiant energy filter therein for protecting an operator from potentially damaging radiant energy being emitted from a workpiece, said kit comprising at least one filter plate portion for use in said aperture so as to provide a first viewing region through which said operator may safely view said workpiece during activities generating potentially damaging radiant energy, and a second viewing region adjacent said first viewing region for viewing said workpiece during activities not generating potentially damaging radiant energy, and a set of instructions for the installation of said kit thereby to allow said operator to view said workpiece through either one of said viewing areas without the need to remove said welding helmet, said helmet further including a first filter plate portion which is substantially equally sized with said aperture, said kit further comprising a second filter plate portion positioned adjacent said first filter plate portion and corresponding with said first viewing region, said first filter plate portion further extending into a region corresponding to said second viewing region, whereby said first and second filter plate portions together have a sufficient filtering index to provide said protection, further comprising positioning means for releasably positioning said second filter plate portion relative to said first filter plate portion, said positioning means further comprising a tape fastener arrangement, comprising a first tape fastener attached to said first filter plate portion and a second tape fastener complementary to said first tape fastener and attached to said second filter plate portion.

* * * * *